United States Patent
Borgert et al.

(10) Patent No.: US 7,907,989 B2
(45) Date of Patent: Mar. 15, 2011

(54) IMAGING SYSTEM FOR INTERVENTIONAL RADIOLOGY

(75) Inventors: Jörn Borgert, Hamburg (DE); Jörg Sabczynski, Norderstedt (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 1320 days.

(21) Appl. No.: 10/560,686

(22) PCT Filed: Jun. 9, 2004

(86) PCT No.: PCT/IB2004/050869
§ 371 (c)(1),
(2), (4) Date: May 4, 2006

(87) PCT Pub. No.: WO2004/110271
PCT Pub. Date: Dec. 23, 2004

(65) Prior Publication Data
US 2006/0251300 A1 Nov. 9, 2006

(30) Foreign Application Priority Data
Jun. 16, 2003 (EP) .................................... 03101751

(51) Int. Cl.
*A61B 5/05* (2006.01)
*G06K 9/00* (2006.01)
(52) U.S. Cl. ........................................ 600/424; 382/128
(58) Field of Classification Search .................. 600/424
See application file for complete search history.

(56) References Cited

U.S. PATENT DOCUMENTS

| 5,211,165 | A | * | 5/1993 | Dumoulin et al. | 600/410 |
| 5,671,739 | A | * | 9/1997 | Darrow et al. | 600/424 |
| 5,906,618 | A | * | 5/1999 | Larson, III | 606/108 |
| 6,052,610 | A | | 4/2000 | Koch | |
| 6,473,635 | B1 | | 10/2002 | Rasche | |
| 6,731,966 | B1 | * | 5/2004 | Spigelman et al. | 600/407 |
| 2002/0049375 | A1 | | 4/2002 | Strommer et al. | |
| 2002/0193675 | A1 | * | 12/2002 | Rathjen | 600/405 |

FOREIGN PATENT DOCUMENTS

| EP | 1388322 A1 | 2/2004 |
| WO | 9605768 A1 | 2/1996 |
| WO | 2004110271 A1 | 12/2004 |

* cited by examiner

*Primary Examiner* — Eric F Winakur
*Assistant Examiner* — Hien Nguyen
(74) *Attorney, Agent, or Firm* — Yan Glickberg

(57) ABSTRACT

The invention relates to a system and an imaging method for visualizing areas (2) in a moving environment within the body of a patient (1), wherein the position of one or more markers, which are connected to an interventional device (4), is determined and used to determine the position of the areas (2) and/or of the interventional device (4) in images (6) which are recorded of the areas (2) and of their environment. According to the invention, the markers used are active locators which independently of the method used to record the images (6) generate data or signals for determining their position. Such an imaging method, which preferably uses electromagnetic locators, allows a considerably more robust representation of the visualized areas (2), with elimination of movements, than is possible using passive markers.

19 Claims, 1 Drawing Sheet

IMAGING SYSTEM FOR INTERVENTIONAL RADIOLOGY

Figure 1:
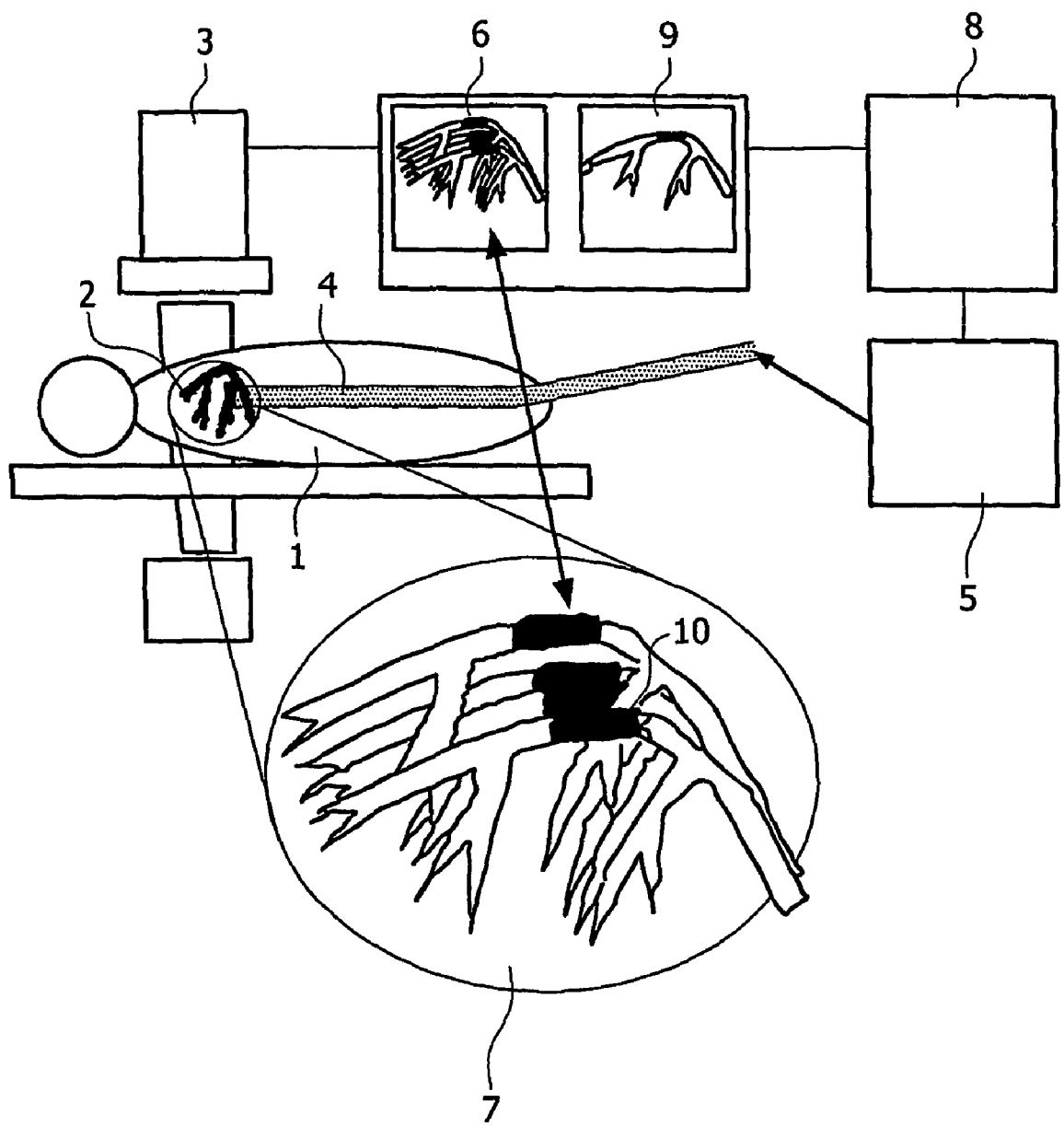

The invention relates to an imaging system and method for visualizing areas in a moving environment within the body of a patient, wherein the position of one or more markers, which are connected to an interventional device, is determined and used to determine the position of the areas and/or of the interventional device in images which are recorded of the areas and of their environment.

Moreover, the invention relates to a record carrier with software for carrying out the method and an interventional device for the system.

The aforementioned systems and methods make it possible to eliminate the movements of the visualized areas in a sequence of successive images and to represent or actually make visible in the image the interventional device inserted into the body and also the areas of the body that surround said interventional device, in a virtually motionless manner and with an improved quality.

Within the context of medical examination and therapy methods, in which catheters, stents or similar devices are inserted into the blood vessels of a patient, e.g. in interventional angiography, the imaging method used therein is of critical importance. In order for example to direct a stent to the correct position or to verify the correct positioning, the treating physician requires a representation of the relevant vessels and/or of the stent that is as clear and as detailed as possible.

The problem arises here that the relevant vessels are usually not at rest but rather are moving. Thus, during implantation of a stent in the region of the heart, even if the patient is not moving at all, the movement of the stent itself must be taken into account together with the further associated devices, the movement of the coronary arteries under the influence of the heartbeat and also the movement of the entire organ under the influence of the patient's breathing. These movements make it extremely difficult to place a stent correctly under X-ray fluoroscopic control, with there moreover being a risk that an incorrectly placed stent may cause thrombosis and thus cut off the blood flow.

In order to solve this problem, according to the prior art use is usually made of radio-opaque passive markings on the interventional devices inserted into the patient's body, in order to be able in this way to locate the objects of interest in a moving image. By using such markers, the movements of the vessels may be compensated and the objects and areas which are of interest to the treating physician can thus be amplified. The use of radio-opaque markings is based on the fact that these appear in the X-ray image recorded of the patient as objects that can be clearly distinguished from the surrounding environment.

However, one disadvantage of this prior art that has been found is that besides the radio-opaque markers, there are often other structures within an image which exhibit a strong contrast. Other objects which appear similar to the markers in the X-ray image may have a disruptive effect. Correspondingly, under some circumstances it is difficult to distinguish the markers from these objects in the image. This applies in particular in the case of automatic determination of the position of the markers, as is necessary in order to compensate the movements of the visualized areas. In general, the known locating methods suffer under the poor contrast and the high level of noise in the recorded X-ray images. Although various methods are known from the prior art which can be used to improve the visualization, such as temporal integration of successive images for example, the fundamental problem of it being difficult to identify the radio-opaque markers nevertheless remains.

A further problem is that the contrast agents frequently used to improve the visualization of vascular structures are toxic, and hence the length of time for which the patient is exposed to the contrast agents should be minimized. For this reason too, it is an object to develop a method which further improves the visualization of areas around the device inserted into the patient's body, said areas being relevant to the treatment.

A system for visualizing areas in a moving environment within the body of a patient comprises at least one data processing unit (computer) and optionally further components like those that are disclosed in the dependent claims, for example a display unit, an interventional device, an imaging system and the like. The data processing unit is adapted to determine the position of the areas and/or of an interventional device in images which are recorded of the areas and of their environment, said determination being based on at least one measured position of at least one active locator connected to the interventional device.

The system therefore makes use of markers that are active locators which independently of the method used to record the images generate data or signals for determining their position.

The process of locating the markers and thus also the device inserted into the body is carried out independently of the image recording device by an independent locating system. Within the context of the invention, active locators are thus those locators in which determination of the position in space takes place independently of the imaging of the locators in the recorded images, namely by means of devices used specifically for position determination. Active locators based on various modes of operation are known from the prior art. For the use according to the invention, those which operate on an electromagnetic basis are especially suitable. However, the use of locators which operate optically or acoustically is also conceivable.

The active locators are used to determine the position of a certain point, e.g. the tip of a device inserted into the body, in the coordinate system of the active locators. Moreover, images of the structures of interest are recorded and placed in relation to the coordinate system of the active locators. In order to place the position of the markers in relation to the recorded images, at least one common reference point at a certain point in time is required. Furthermore, the markers serve as "trackers" in order to keep track of a certain area within the body of the patient in the images.

In order to place the coordinate system of the active locators in relation to the recorded images, they may also be used in combination with radio-opaque markings. If the relative positions of the radio-opaque markings and of the active locators on the interventional device are known, a calibration can be carried out in a simple manner, said calibration providing the link between the images and the position of the active locators. Since, once calibration is complete, the position determination for the imaging method of the system takes place by means of active locators, the robustness of the imaging is considerably improved.

The recording of the images for visualizing the relevant objects and structures may in principle take place by at least one imaging device that belongs to the system and that generates images according to conventional methods such as X-ray projection, computer tomography (CT), magnetic resonance tomography (MR), positron emission tomography (PET), optical coherence tomography (OCT), single photon emission computer tomography (SPECT), endoscopy or ultrasound. In particular, use may be made of a so-called C-arm X-ray device as is often used in the case of catheter examinations, the arms of which are passed above and/or below the body of the patient.

The interventional device which according to the invention is provided with active locators serving as markers may also belong to the system and may typically be a catheter, a balloon catheter, a stent delivery catheter or a guidewire. It is thus essentially one of those devices which according to the prior art may be provided with radio-opaque markings.

The system and the method are of particular significance in respect of examinations and treatments in the cardiovascular domain, such as for example the placing of a stent in a coronary vessel, in PTCA (percutaneous transluminal coronary angioplasty) or in the intraluminary removal of obstructions. A further field of use is the closure of aneurysms. Although the method according to the invention and also the system are primarily provided for use in the cardiovascular domain, other fields of use are obviously not ruled out, such as for example the treatment of intracranial aneurysms, the carrying out of biopsies or ablations.

The images of the structures are preferably recorded at the same time as the position of the active locators is determined. Correspondingly, the position of the object or area that is to be visualized can be detected and kept constant in a sequence of temporally successive images by virtue of the data processing unit for each individual image, so that the movements in the successive images are eliminated. For this purpose, the processing system, which receives the information about the respective position of the markers from the locating system for the active locators, can also correct the images in terms of their position. In this case, the markers serve quasi as fixed points in the successive images. The temporally successive images are expediently displayed on a display unit or screen in processed form such that the imaged structures appear to the treating physician to be practically motionless.

As an alternative, however, it is also possible to relate the position of the markers connected to the interventional device that is inserted into the body with reference images recorded prior to treatment. In particular, it is possible to produce so-called "road maps" prior to the actual treatment, said road maps being images of the vessels taken while using contrast agents. There is thus no need to administer contrast agents during the actual treatment, in order in this way to minimize the side effects for the patient. When relating the marker positions to road maps, instead of conventional 2D images use may also be made of 3D images which provide the treating physician with even more detailed information by adding a further dimension. The recording of 3D images may take place for example by means of MR (magnetic resonance), CT (computer tomography) or 3D-XRA. Alternatively, 3D images may also be generated by combining individually recorded 2D images.

Of course, 3D images can also be recorded at the same time as the markers are located. In a sequence of temporally successive images, a quasi-4D representation is obtained, with time representing a further dimension.

The active locators used may supply, besides the position, also information about the orientation of the device inserted into the body of the patient. Depending on the number and type of locators used, different information can thus be extracted via the active locating system. Thus, when using a marker which exclusively supplies information about the position, only information about the translation of the inserted device is obtained. On the other hand, when using a marker which supplies information about both position and orientation, information about translation and rotation of the interventional device is obtained. By adding in each case one further marker, information about expansion and twisting can also be obtained where appropriate. For instance, when using a stent which is provided to expand a blood vessel that is to be kept open, information about the expansion of the stent may be of particular importance. In principle, the number of items of information that can be extracted may be further expanded at will by using as many locators as desired and relating them to 3D images in order to optimally adapt a certain model to the conditions.

Besides the use of active locators which supply information about position and orientation, the use of markers which make it possible to obtain information about the shape of the inserted interventional device is also possible. This allows further refinement of the processed images.

Besides the elimination of movement, further measures to optimize the representation may be provided within the visualized areas, said further measures being referred to below as "local boosting". Thus, the visualized areas and structures may be optically amplified by increasing the contrast between various gray stages, in order to optimize the representation. It is furthermore possible, when inserting a tubular object such as a stent which is connected to active locators which supply information via the center line of the stent, e.g. between a start point and an end point, to optically emphasize the object between these points in the representation. Such an emphasis makes the areas and devices that are relevant for the physician particularly visible.

A further method of improving the visualization of the areas observed is the carrying out of a temporal integration over a sequence of successive images. This method is based on the fact that the background of the objects and vessels that are fixed in the image moves in a sequence of images so that irregularities which occur in this background average out whereas the areas that are fixed in the image are amplified relative to the background. Viewed overall, the relevant areas are thus emphasized to an even greater extent relative to the background in the representation.

According to one preferred embodiment of the system according to the invention, a number of interventional devices for insertion into the body of the patient, for example a stent delivery catheter, the catheter of the balloon used to expand the stent and the guidewire used to direct the catheter, are provided with active locators serving as markers, so that during treatment the user can select between the various active locators as required in order thus to spatially fix different areas in the representation of the recorded images. It may thus be useful for the treating physician for example to focus at the start of a treatment on the tip of a guidewire, then as the treatment progresses to focus on the tip of a catheter and during placement of the stent to focus on the latter itself. In this way, precisely the correct area can be shown enlarged or in a spatially fixed manner at the correct point in time in each case.

The active locators used for the applications described here are preferably those which operate electromagnetically. Such systems for determining the position of an instrument within the body of a patient are commercially available. Such an EMPMS (electromagnetic position measurement system) usually consists of a device outside the patient, which generates a magnetic field, and field sensors which are placed in the patient. The field generator generates a magnetic field of known size, which varies with the time and position. The field sensors consist of one or more small coils or Hall sensors which make it possible to determine the size of the magnetic field or the change therein in relation to the position of the sensor. Since the magnetic field coming from the field generator is known per se, the respectively prevailing local field at a certain time and at a certain location can also be calculated. By means of comparison with the local fields determined by the field sensors, the positions can thus be determined.

An electromagnetic-based method of determining the position of a catheter in three-dimensional space is also described in U.S. Pat. No. 6,052,610. In said method, a small rotating permanent magnet is attached to the tip of the catheter, the magnetic field of which magnet is detected by magnetic field sensors and evaluated.

According to a preferred embodiment the system comprises a device for recording images of areas in a moving environment within the body of a patient, a unit for determining the position of active locators which are connected to interventional devices inserted into the body, and image processing means which use the determined position of the active locators to determine in the recorded images the position of relevant areas and/or of the interventional device inserted into the body. The image processing means is the data processing unit (computer) which evaluates and further processes the data transmitted to it by the locating system and by the image recording device. For displaying the images, the system preferably has one or more screens on which the focused area is displayed. In addition, the unprocessed images can also be shown on further screens.

In an imaging method for visualizing areas in a moving environment within the body of a patient, the position of one or more active locators, which are connected to an interventional device, is determined and used to determine the position of the areas and/or of the interventional device in images which are recorded of the areas and of their environment, wherein the active locators independently of the method used to record the images generate data or signals for determining their position.

Moreover, a record carrier is provided on which a computer program for visualizing areas in a moving environment within the body of a patient is stored, said program being adapted to execute a method of the aforementioned kind.

Finally, an interventional device is provided with at least one active locator, particularly a stent, a catheter, a balloon or a guidewire.

The method, the record carrier, and the interventional device may be executed with or are suited for a system of the kind described above. For more information on the details, advantages and improvements of them reference is therefore made to the description above.

The invention will be further described with reference to an example of embodiment shown in the drawing to which, however, the invention is not restricted.

FIG. 1 shows a schematic diagram of a system for carrying out the method according to the invention.

A stent 10 is to be placed into a vessel 2 in the body of the patient 1, which stent is inserted into the patient 1 via an interventional device 4. The device 4 is equipped with active locators as markers, the position of which can be determined via a locating system 5. At the same time, a sequence of live images 6 is recorded with the aid of an image recording device 3, in this case a C-arm X-ray device. The live images 6, which are shown in a detailed enlargement 7, vary over time since the vessel 2 and hence also the stent 10 that is inserted into the vessel are continually moving. However, with the aid of the data processing system 8, which receives the necessary data from the locating system 5 and the image recording device 3, the position of an active locator connected to the device 4 which is determined by the locating system 5 is used to serve as a fixed point in a sequence of temporally successive live images 6. The representation of the vessel 2, which is changing over time in the detailed enlargement 7, is thus shown in the representation 9 with the movement having been eliminated. At the same time, further image processing methods such as temporal integration are used to make the background in the representation 9 weaker and by contrast to make the vessel 2 and the stent 10 appear emphasized. The clear representation 9 of the vessel 2 with the stent 10 allows the treating physician to navigate the device 4 more easily and place the stent 10 correctly.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An apparatus for visualizing an area in a moving environment within a body of a patient associated with an interventional device to which radio-opaque markings have been applied, the system comprising:
   a data processing unit configured to:
   reconstruct image data into a series of images with each image of the series of images depicting the visualized area of the patient, the radio-opaque markings applied to the interventional device, and at least one of an active locator affixed to the interventional device in a fixed, known relationship to the radio-opaque markings and the interventional device,
   display the series of images depicting the visualized area on a display, and
   use the depictions of the radio-opaque markings and determined locations of the active locator to keep a position of a selected region of the visualized area constant in the series of images.

2. The apparatus of claim 1, further including:
   an imaging system which records a temporally successive sequence of images depicting at least the interventional device, the radioopque markings, and the visualized areas.

3. The apparatus of claim 1, further including:
   a display unit which displays the images and/or a representation of the images.

4. The apparatus of claim 1, further including:
   at least one imaging device which records said images, the imaging device including at least one of a device for X-ray projection, computer tomography, magnetic resonance tomography, positron emission tomography, optical coherence tomography, single photon computer tomography, endoscopy or ultrasound.

5. The apparatus of claim 1, wherein the images are recorded at the same time as the position of the active locator is measured.

6. The apparatus of claim 1, wherein the data processing unit is further configured to optically emphasize the visualized areas in the recorded images.

7. The apparatus of claim 1, wherein the data processing unit is further configured to carry out a temporal integration over a sequence of successive images.

8. The apparatus of claim 1, wherein the interventional device includes at least one of a stent, a catheter, a balloon, and a guidewire.

9. The apparatus of claim 1, wherein the active locator includes an electromagnetic locator.

10. The apparatus of claim 1, wherein the active locator supplies, besides the position, also information about at least one of an orientation and shape of the interventional device.

11. The apparatus of claim 1, further including:
an interventional instrument including radio-opaque markings and at least one active locator affixed in a fixed, known relationship.

12. An imaging method for visualizing an area in a moving environment in a patient, the method comprising:
positioning an interventional instrument to which an active locator and a radio-opaque markings are attached internally in the visualized area of the moving environment of the patient;
generating radiographic image data of the visualized area of the moving environment of the patient including the radio-opaque markings;
determining locations of the active locator as the visualized area of the moving environment moves;
from the image data of the radio-opaque markings and the determined locations of the active locator, determining positions of the interventional instrument in the visualized area;
generating a series of images from the radiographic image data depicting the visualized area of the moving environment of the patient, the radio-opaque markings, and the active locator and the interventional instrument;
displaying the series of images of the visualized area on a display; and
a processor configured to use the radio-opaque markings and the determined positions of the active locator to keep the position of the active locator and the visualized area constant in the series of images.

13. A record carrier on which a computer program for visualizing areas in a moving environment within the body of a patient is stored, said program being adapted to execute a method according to claim 12.

14. The method of claim 12, wherein a relative position of the radio-opaque markings and the active locators are known.

15. A system for visualizing an area in a moving environment within a patient, the system comprising:
an interventional instrument including radio-opaque markings and at least one active locator affixed in a fixed, known relationship;
a display on which a series of images depicting the visualized area is displayed;
a radiographic imaging system which generates image data of the visualized area;
a locating system which determines locations of the active locator when the interventional instrument is disposed in the visualized area;
a data processing unit which uses the determined active locator locations to reconstruct the image data into the series of images of the visualized area with each image of the series of images depicting the visualized area of the patient, the radio-opaque markings and at least one of the at least one active locator and the interventional instrument, and using the depictions of the radio-opaque markings and the determined locations of the active locator to keep a position of at least a region of the visualized area adjacent the at least one active locator constant in the series of images.

16. The system of claim 15, wherein the interventional instrument includes a stent and a stent delivery catheter and wherein the data processing unit further depicts the stent in the reconstructed series of images and causes the series of images to be displayed with the stent kept in a constant position in each image of the series of images.

17. The system of claim 16, wherein the data processing unit uses the known relationship between the at least one active locator and the radio-opaque markings to determine information about expansion of the stent and depict the determined information about the expansion of the stent in the displayed series of images.

18. The system of claim 15, wherein the data processing unit uses the known relationship between the at least one active locator and radio-opaque markings to determine orientation and rotation of the interventional instrument.

19. The system of claim 15, wherein the data processing unit further uses the known relationship between the at least one active locator and the radio-opaque markings to link the locations of the at least one active locator and the images of the series more accurately.

* * * * *